US007348025B2

(12) United States Patent
Knight et al.

(10) Patent No.: US 7,348,025 B2
(45) Date of Patent: *Mar. 25, 2008

(54) SMALL PARTICLE LIPOSOME AEROSOLS FOR DELIVERY OF ANTICANCER DRUGS

(75) Inventors: J. Vernon Knight, Houston, TX (US); Nadezhda Koshkina, Houston, TX (US); Brian Gilbert, Houston, TX (US); Claire F. Verschraegen, Albuquerque, NM (US)

(73) Assignee: Research Development Foundation, Carson City, NV (US)

( * ) Notice: Subject to any disclaimer, the term of this patent is extended or adjusted under 35 U.S.C. 154(b) by 769 days.

This patent is subject to a terminal disclaimer.

(21) Appl. No.: 10/663,573

(22) Filed: Sep. 16, 2003

(65) Prior Publication Data

US 2006/0204447 A1    Sep. 14, 2006

Related U.S. Application Data

(63) Continuation-in-part of application No. 09/969,374, filed on Oct. 1, 2001, now abandoned, which is a continuation of application No. 09/353,496, filed on Jul. 15, 1999, now abandoned.

(51) Int. Cl.
*A61K 31/4745* (2006.01)
*A61K 9/127* (2006.01)
*A61L 9/04* (2006.01)

(52) U.S. Cl. ............... 424/450; 424/45; 514/283

(58) Field of Classification Search ............. 424/450
See application file for complete search history.

(56) References Cited

U.S. PATENT DOCUMENTS

| 4,963,367 | A | | 10/1990 | Ecanow ............ 424/485 |
| 5,049,388 | A | * | 9/1991 | Knight et al. ...... 424/450 |
| 5,277,914 | A | | 1/1994 | Szoka, Jr. .......... 424/450 |
| 5,366,737 | A | | 11/1994 | Eppstein et al. .... 424/450 |
| 5,422,344 | A | * | 6/1995 | Priel et al. .......... 514/50 |
| 5,552,156 | A | | 9/1996 | Burke ............... 424/450 |

(Continued)

FOREIGN PATENT DOCUMENTS

DE    4430593 C2    8/1994

(Continued)

OTHER PUBLICATIONS

Burke, "Lipid bilayer partitioning and stability of camptothecin drugs," *Biochemistry*, 32:5352-5364, 1993.

(Continued)

*Primary Examiner*—Michael P. Woodward
*Assistant Examiner*—Aradhana Sasan
(74) *Attorney, Agent, or Firm*—Fulbright & Jaworski L.L.P.

(57) ABSTRACT

Provided herein is a method of treating primary lung cancer or metastatic cancer to the lung in an individual by delivering at least once to the respiratory tract of the individual via inhalation a nebulized liposomal aerosol comprising a dilauroylphosphatidylcholine liposome containing camptothecin or a derivative thereof in an amount sufficient to deliver a pharmacologically effective dose of the camptothecin or its derivative to treat the cancer. Also provided is a nebulized liposomal aerosol comprising the DLPC containing the camptothecin or its derivative and a method of making the liposome-drug comprising the aerosol.

11 Claims, 10 Drawing Sheets

U.S. PATENT DOCUMENTS

| | | | | |
|---|---|---|---|---|
| 5,736,156 | A | * | 4/1998 | Burke ................... 424/450 |
| 5,958,378 | A | | 9/1999 | Waldrep et al. ............ 424/45 |
| 6,090,407 | A | * | 7/2000 | Knight et al. ............. 424/450 |
| 6,346,233 | B1 | | 2/2002 | Knight et al. .............. 424/45 |
| 2004/0208935 | A1 | * | 10/2004 | Giovanella et al. ......... 424/489 |

FOREIGN PATENT DOCUMENTS

| | | |
|---|---|---|
| EP | 0349127 | 1/1990 |
| WO | WO 9318751 | 3/1993 |
| WO | WO 9426253 | 5/1994 |
| WO | WO 9605821 | 8/1995 |
| WO | WO 9619199 | 12/1995 |
| WO | WO 98/00111 | 1/1998 |

OTHER PUBLICATIONS

Hinz et al., "Pharmacokinetics of the in Vivo and in Vitro Conversion of 9-Nitro-20(S)-camptothecin to 9-Amino-20(S)-camptothecin in Humans, Dogs, and Mice," *Cancer Res.*, 54:3096-3100, 1994.

Lesueur-Ginot et al., "Homocamptothecin, an E-ring modified camptothecin with enhanced lactone stability, retains topoisomerase I-targeted activity and antitumor properties," *Cancer Res.*, 59:2939-2943, 1999.

Mi et al., "Reduced albumin binding promotes the stability and activity of topotecan in human blood," *Biochemistry*, 34:13722-13728, 1998.

Ozer, "Stability studies of 5-FU liposomes," *Drug Targeting Delivery*, 1:151-160, 1992.

Schreier et al., "Pulmonary delivery of liposomes," *J. Controlled Release*, 24:209-223, 1993.

Sugarman et al., "Lipid-complexed camptothecin: formulation and initial biodistribution and antitumor activity studies," *Cancer Chemother Pharmacol.*, 37:531-538, 1996.

Verschraegen et al., "A phase I clinical and pharmacological study of oral 9-nitrocamptothecin, a novel water-insoluble topoisomerase I inhibitor," *Anti-Cancer Drugs*, 9:36-44, 1998.

Verschraegen et al., "Alternative administration of camptothecin analogues," *Ann NY Acad. Sciences*, 922:237-246, 2000.

Waldrep et al., "Cyclosporin A liposome aerosol: particle size and calculated respiratory deposition," *Int. J. Pharaceutics*, 97:205-212, 1993.

Waldrep et al., "Nebulized glucocorticoids in liposomes: aerosol characteristics and human dose estimates," *J. Aerosol Med.*, 7:133-145, 1994.

Weibel, "Geometry and dimensions of airways of conductive and transitory zones," In Morphometry of the Human Lungs, NY: Academic Press Inc., 110-140, 1963.

Zamboni et al., "Phase I and pharmacokinetic (PK) study of intermittently administered 9-nitro-campothecin (9NC, Rubitecan) in patients with advanced malignancies," *Proc. Am. Soc. Clin. Oncol.*, A411, 2001.

"Chiron submits new drug application for pulminiq; inhaled form of cyclosporine could be first immunosuppressant indicated for chronic lung-transplant rejection," www.drugs.com/nda/pulminiq_041014.html, Sep. 14, 2006.

Abang et al., "The clinical pharmacology of topoisomerase I inhibitors," *Sem Hematol*, 35:13-21, 1998.

Ahmed et al., "Influence of route of administration on [3h]-camptothecin distribution and tumor uptake in CASE-bearing nude mice: whole-body autoradiographic studies," *Cancer Chemother Pharmacol.*, 39:122-130, 1996.

Anderson, "Delivery systems for immunomodulatory proteins and peptides," *BioDrugs*, 7:51-65, 1997.

Burckart et al., "Lung deposition and pharmacokinetics of cyclosporine after aerosolization in lung transplant patients," *Pharmaceutical Research*, 20:252-256, 2003.

Chourpa et al., "Modulation in kinetics of lactone ring hydrolysis of camptothecins upon interaction with topoisomerase I cleavage sites on DNA," *Biochem*, 37:7284-7291, 1998.

Fresta et al., "Evaluation and optimization of liposomes as delivery device for methotrexate," *Pharmazie*, 47:926-929, 1992.

Garcia-Carbonero et al., "Current perspectives on the clinical experience, pharmacology, and continued development of the camptothecins," *Clin. Cancer Res.*, 8:641-661, 2002.

Giovanella et al., "Complete growth inhibition of human cancer xenografts in nude mice by treatment with 20-(S)-camptothecin," *Cancer Res.*, 51:3052-3055, 1991.

Hallman et al., "Inositol supplementation in premature infants with respiratory distress syndrome," *N. Eng. J. Med.*, 326:1233-1239, 1992.

Hausheer et al., "Karenitecins: a novel, potent class of oral highly lipophillic topo I inhibitors," *Proc. Annu. Meet. Am. Asoc. Cancer Res.*, 38:A1526, 1997.

Hertzberg et al., "Modification of the hydroxy lactone ring of camptothecin: inhibition of mammalian topoisomerase I and biological activity," *J. Medic. Chem.*, 32:715-720, 1989.

Hochster et al., "Phase I trial of low-dose continuous topotecan infusion in patients with cancer: an active and well-tolerated regimen," *J. Clin. Oncol.*, 12:553-559, 1994.

Iacono et al., "Aerosol cyclosporin therapy in lung transplant recipients with bronchiolitis obliterans," *Eur. Respir. J.*, 23:384-390, 2004.

Kim et al., "Pharmacodynamics of insulin in polyethylene glycol-coated liposomes," *Int. J. Pharm.*, 180:75-81, 1999.

Knight et al., "New approaches in aerosol drug delivery for the treatment of asthma," in Allergy and Allergic Diseases, Kay (ed), Blackwell Publications, Oxford, England, I:730-741, date unknown.

\* cited by examiner

Fig. 8

SMALL PARTICLE LIPOSOME AEROSOLS FOR DELIVERY OF ANTICANCER DRUGS

CROSS-REFERENCE TO RELATED APPLICATIONS

This application is a continuation-in-part of continuing application U.S. Ser. No. 09/969,374, filed Oct. 1, 2001, which is a continuation of divisional application U.S. Ser. No. 09/353,496, filed Jul. 15, 1999, now abandoned, which claims priority to non-provisional application U.S. Ser. No. 08/933,254, filed Sep. 23, 1997, now issued as U.S. Pat. No. 6,090,407 on Jul. 18, 2000.

BACKGROUND OF THE INVENTION

1. Field of the Invention

The present invention relates generally to the field of pharmacology and cancer treatment. Specifically, the present invention provides methods of cancer treatment using nebulized formulations of aerosolized liposomes containing camptothecins for delivery to the respiratory tract.

2. Description of the Related Art

Small particle liposome aerosol treatment consists of lipid-soluble or water-soluble anti-cancer drugs incorporated into liposomes, which are administered from aqueous dispersions in a jet nebulizer as disclosed in U.S. Pat. No. 5,049,388. Aerosols of 1-3 μm mass median aerodynamic diameter, generated upon nebulization, enable targeted delivery onto surfaces of the respiratory tract. The deposited liposomes subsequently release drug locally within the lung or into the blood circulation with delivery to extra-pulmonary tissue. If the drug is lipid soluble, it will associate with the lipid molecules in a manner specific to the lipid employed and to the anti-cancer drug employed and, possibly, may be modified further by various soluble constituents included in the suspending aqueous medium. Such soluble constituents may include buffering salts and possibly inositol to enhance the synthesis and secretion of surfactant phospholipid in lung tissue and to minimize respiratory distress already present or that which might result from the aerosol treatment (31). If the drug is water soluble, it may be incorporated by appropriate procedures in aqueous vesicles that exist in concentric spaces between lipid bilayers or lamellae of the multilamellar liposome. Unilamellar liposomes may be prepared; however, their capacity to entrap either lipid-soluble or water-soluble drugs is diminished since entrapment is restricted to one central vesicle.

Aerosol water droplets may contain one or more drug-liposomes. Nebulization shears liposomes to sizes readily discharged from the nozzle of the nebulizer. Liposomes up to several microns in diameter are typically sheared to diameters of less than 500 nm, and may be considerably smaller than that depending on the operating characteristics of the nebulizer and other variables. Shearing of water-soluble drugs contained in liposomes will release appreciable amounts of the water-soluble compound, perhaps 50 percent. This is not a contraindication to their use, but rather two forms of the drug preparation are administered. The effect includes the therapeutic effect that would be produced by both forms if either form had been given alone. Many other details of liposome aerosol treatment are described in U.S. Pat. No. 5,049,388. Moreover, it is also possible to incorporate more than one drug in an aerosol liposome treatment, either by mixing different drug-containing liposomes or by using liposomes wherein the drugs have been combined and incorporated together into liposomes.

One such drug is camptothecin (CPT), an inhibitor of topoisomerase-I, which is a plant alkaloid isolated from *Camptotheca acuminata* in 1966. Inhibitors of topoisomerase-I are potent antineoplastic drugs. Human cancer cells grown as xenografts in nude mouse models are greatly inhibited or may be eradicated after treatment with most camptothecin analogs (15). In clinical settings, camptothecins have been less effective (16). In comparison to mice, human metabolism of camptothecins yields a poor therapeutic index, which could explain the low response rate in cancer patients.

The anti-tumor activity of several of the camptothecins is diminished following dissolution in aqueous media. This is due to a hydrolyzable alpha-hydroxy lactone ring (ring E) which opens upon hydrolysis. The change results from acyl cleavage yielding the biologically inactive carboxylate form of the molecule. The lactone ring form of the drug is sheltered in liposomes, but pharmacokinetics of camptothecins in the presence of human serum albumin favors the inactive carboxylate form or open E-ring (17). This leads to rapid conversion of lactone to carboxylate in the presence of human serum albumin and, thus, to loss of anti-cancer activity.

Attempts to improve the therapeutic index of camptothecins using continuous infusion and oral administration have had limited success (18-20). Furthermore, increasing the exposure of cancer cells to the active lactone form or designing analogs with increased lactone stability to use in a clinical setting have not resulted in significant clinical improvement (21-26). In previous clinical studies of oral administration, the main toxicity profile of 9-NC was hematologic with anemia and neutropenia and gastrointestinal with nausea, vomiting and anorexia (28,29). Another difficult side effect of oral administration was chemical cystitis with hematuria (29).

The inventors have recognized a need in the art for methods of treating cancer in a human using camptothecins that avoids interaction with serum albumin or other constituents to preserve the anti-cancer effect of the camptothecins with significant reduction in toxicity. Specifically, the prior art is deficient in methods of treatment using formulations of aerosolized liposomes containing camptothecins that are deposited within the lungs on alveolar surfaces to effect treatment of the cancer. The present invention fulfills this long-standing need and desire in the art.

SUMMARY OF THE INVENTION

The present invention is directed to a method for treating a primary lung cancer or a metastatic cancer to the lung by delivering at least once to the respiratory tract of the individual via inhalation a nebulized liposomal aerosol comprising a dilauroylphosphatidylcholine liposome containing camptothecin or a derivative thereof in an amount sufficient to deliver a pharmacologically effective dose of the camptothecin or its derivative to treat the cancer.

The present invention is directed further to a nebulized liposomal aerosol comprising dilauroylphosphatidylcholine and camptothecin or a derivative thereof suitable for delivery of the camptothecin or its derivative to the respiratory tract of an individual upon inhalation of the nebulized liposomal aerosol. The concentration of the camptothecin or its derivative in the dilauroylphosphatidylcholine liposome does not exceed 1.0 mg/ml. The present invention is also directed to a method of producing the dilauroylphosphatidyl-camptothecin or derivative thereof liposome comprising the nebulized liposomal aerosol.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 8 demonstrates the total 9-nitrocampthecin plasma pharmacokinetics in 5 patients of cohort 1 treated with DPLC-9NC liposomal aerosol by mouth-only breathing.

DETAILED DESCRIPTION OF THE INVENTION

Figure 1:
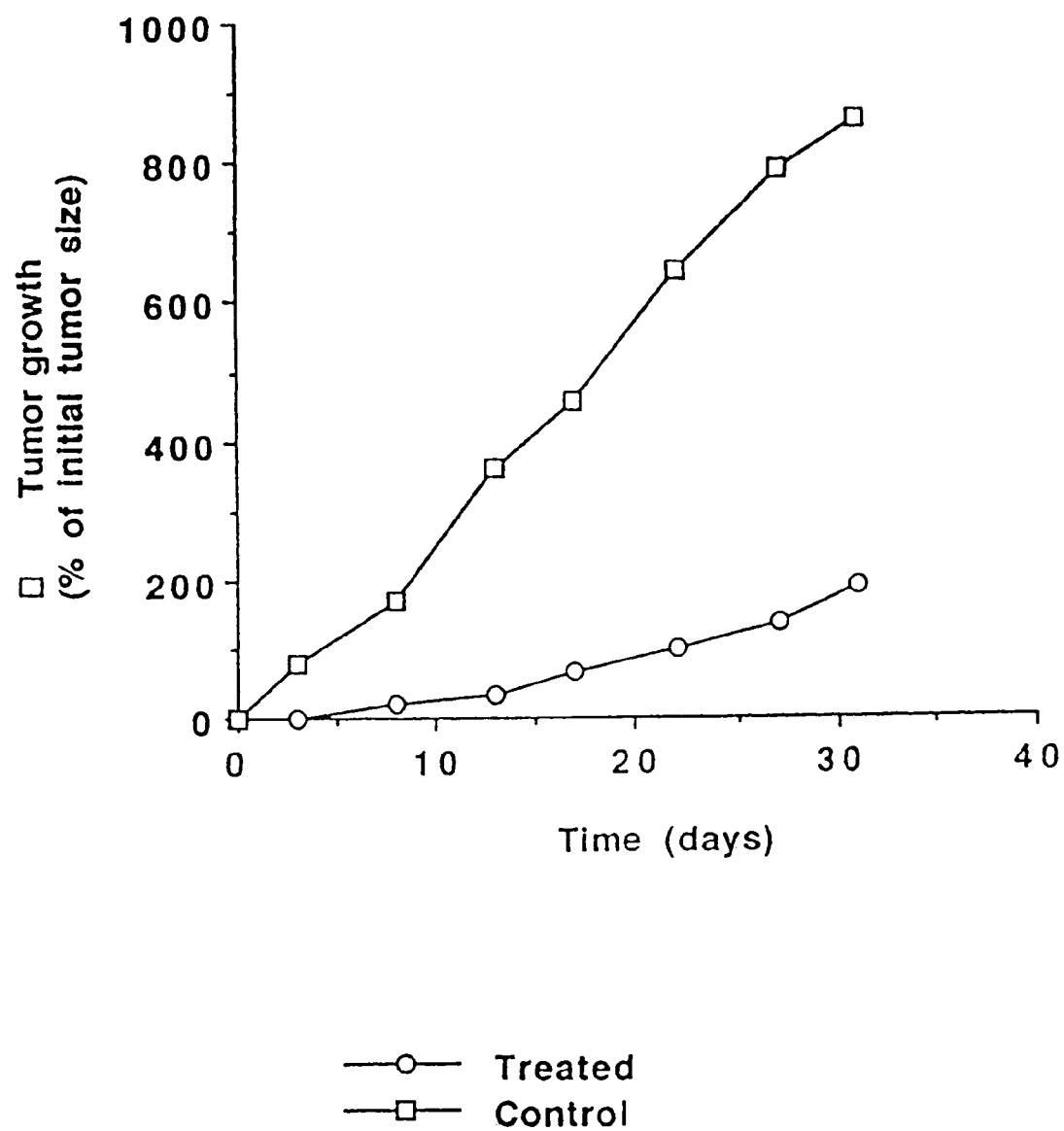
FIG. 1 demonstrates the effect of treatment with 9-NC-DLPC liposome aerosol on xenografted human breast cancer in nude mice.

In one embodiment of the present invention there is provided a method for treating a primary lung cancer or a metastatic cancer to the lung by delivering at least once to the respiratory tract of the individual via inhalation a nebulized liposomal aerosol comprising a dilauroylphosphatidylcholine liposome containing camptothecin or a derivative thereof in an amount sufficient to deliver a pharmacologically effective dose of the camptothecin or its derivative to treat the cancer.

In an aspect of this embodiment the nebulized liposomal aerosol is delivered via an inhalation regimen comprising twice a day for 5 consecutive days within a week for one or more consecutive weeks. In an example of such a regimen the period of consecutive weeks is the first 8 weeks out of a ten week period. Further in this aspect the inhalation regimen may be repeated after week 10 of the regimen. Within this aspect the nebulized liposomal aerosol may be inhaled for 60 minutes during each period of inhalation in the regimen. In any described inhalation regimen the dose of camptothecin or it derivative delivered via inhalation may be about 0.26 mg/m$^2$/day to about 1.04 mg/m$^2$/day.

In all aspects of this embodiment the concentration of the camptothecin or its derivative in the dilauroylphosphatidylcholine liposome comprising the liposomal aerosol does not exceed 1.0 mg/ml. A representative example of such a concentration is 0.4 mg/ml. Also, in all aspects a weight ratio of camptothecin or its derivative to dilauroylphosphatidylcholine in the liposome comprising the liposomal aerosol is about 1:10 to about 1:50 wt:wt.

Additionally, in all aspects of this embodiment the camptothecin derivative may be 9-nitro-camptothecin, 9-amino-camptothecin or 10,11-methylenedioxy-camptothecin. The metastatic cancer may be a sarcoma, a melanoma, lung cancer endometrial cancer, cervical cancer, pancreatic cancer, thyroid cancer or trophoblastic cancer.

In another embodiment of the present invention there is provided a nebulized liposomal aerosol comprising dilauroylphosphatidylcholine and camptothecin or a derivative thereof suitable for delivery of the camptothecin or its derivative to the respiratory tract of an individual upon inhalation of the nebulized liposomal aerosol. The concentration of the camptothecin or its derivative in the dilauroylphosphatidylcholine liposome does not exceed 1.0 mg/ml. A representative example of concentration is 0.4 mg/ml. In all aspects of this embodiment the weight ratios of the camptothecins to dilauroylphosphatidylcholine, the camptothecin derivatives and the metastatic cancers are as described supra.

In an aspect of this embodiment a method of producing the dilauroylphosphatidyl-camptothecin or derivative thereof liposome comprising the nebulized liposomal aerosol is provided. The method comprises the steps of dissolving one of the camptothecins in a volume of DMSO to produced dissolved camptothecin or its derivative, dissolving the dilauroylphosphatidylcholine in an appropriate to solvent to produce dissolved dilauroylphosphatidylcholine and combining the dissolved constituents to produce a solution having a DMSO concentration not exceeding about 5% of the total volume of the solution. The weight ratio of the camptothecin or its derivative to the dilauroylphosphatidylcholine in the solution is in a range of about 1:10 wt:wt to about 1:50 wt:wt of the solution. The solvents are evaporated from the solution to form a powder. The powder is redissolved in sterile water to produce a suspension such that a concentration of the camptothecin or its derivative in the sterile water does not exceed 1.0 mg/ml.

The following terms shall be interpreted according to the definitions set forth below. Terms not defined infra shall be interpreted according to the ordinary and standard usage in the art.

As used herein, the term "aerosols" refers to dispersions in air of solid or liquid particles, of fine enough particle size and consequent low settling velocities to have relative airborne stability (See Knight, V., Viral and Mycoplasmal Infections of the Respiratory Tract. 1973, Lea and Febiger, Phila. Pa., pp. 2). "Liposome aerosols" consist of aqueous droplets within which are dispersed one or more particles of liposomes or liposomes containing one or more medications intended for delivery to the respiratory tract of man or animals (32). The size of the aerosol droplets defined for this application are those described in U.S. Pat. No. 5,049,338, namely mass median aerodynamic diameter (MMAD) of 1-3 μm with a geometric standard deviation of about 1.8-2.2. However, with low concentrations of 9-NC and possibly other camptothecin derivatives, the MMAD may be less than 1 μm, such as 0.8 μm. Based on the studies disclosed by the present invention, the liposomes may constitute substantially all of the volume of the droplet when it has equilibrated to ambient relative humidity.

As used herein, the "Weibel Lung Model" refers to a classification of the structure of the human lungs that recognizes 23 consecutive branchings of the airways of humans. The trachea is labeled 0, bronchi and bronchioles extend through branches 16. These portions of the airways contain ciliated epithelium and mucus glands. Together they constitute the mucociliary blanket. Branchings 17-23 compose the alveolar portion of the lung and do not have a mucociliary blanket. Thus, particles deposited here are not carried up the airway to be swallowed.

As used herein, the terms "20-S-camptothecin", "camptothecin" or "CPT" refers to a plant alkaloid with anti-cancer properties.

As used herein, the terms "9-nitro-camptothecin" or "9-NC", "9-amino-camptothecin" or "9-AC," and "10,11-methylenedioxy-camptothecin" or "MDC" refer to active anti-cancer drugs derived from 20-S-camptothecin that are insoluble in water but are soluble in certain lipid solvents.

As used herein, the terms "dilauroylphosphatidylcholine" or "DLPC" is a lipid used to formulate liposomes.

Provided herein is a method for treating a primary or metastatic lung cancer in an individual by delivering a nebulized DLPC-CPT or -CPT derivative liposomal aerosol to the respiratory tract of the individual via inhalation. A jet nebulizer nebulizes the DLPC-CPT or -CPT derivative liposomes to form a small particle aerosol comprising aqueous dispersions of the DLPC-CPT or -CPT derivative liposomes that subsequently are delivered to the individual upon inhalation. The present invention demonstrates that speedier and more efficient systemic absorption of camptothecin or a derivative thereof is actualized after pulmonary administration by aerosol than is actualized by intramuscular or oral administration. Although not limited to such, the present methods are effective in treating cancers such as sarcomas, melanomas, lung cancer, endometrial cancer, cervical cancer, pancreatic cancer, thyroid cancer or trophoblastic cancer.

It is contemplated specifically that the nebulized liposomal aerosols of the present invention be used for delivery via inhalation of aqueous dispersions of liposomes carrying camptothecin or a derivative thereof to the respiratory tract the individual. Examples of camptothecins used in the present invention are 20-S-camptothecin or camptothecin, 9-nitro-camptothecin, 9-amino-camptothecin or 10,11-methylenedioxy-camptothecin. Camptothecin or its derivatives is delivered in a pharmacologically effective amount; i.e., a total amount that eliminates or reduces the tumor burden of the cancer. To be effective the concentration of the camptothecin or derivative in the dilauroylphosphatidylcholine liposome comprising the liposomal aerosol should not exceed 1.0 mg/ml and preferably is 0.4 mg/ml. Additionally, the weight ratio of the camptothecins to DLPC is within the range of about 1:10 wt:wt to about 1:50 wt:wt, preferably 1:50.

Although the dose and dosage regimen will depend upon the nature of the cancer, i.e., primary or metastatic, the characteristics of the particular camptothecin chosen, e.g., its therapeutic index, the patient, the patient's history and other factors, a person having ordinary skill in this art would readily be able to determine, without undue experimentation, the appropriate dosages. Typically, however, the amount of camptothecin or its derivative administered via inhalation may be in the range of about 0.26 $mg/m^2$/day to about 1.04 $mg/m^2$/day or about 6.7 μg/kg/day to about 26.6 μg/kg/day. The dosage or inhalation regimen may comprise one or two inhalation therapies per day using all or a divided daily dose over a period of consecutive days, e.g., 5, in a week additionally over a period of consecutive weeks such as 8 out of 10 weeks. It is also contemplated that a dosage or inhalation regimen may be repeated.

Treatment using a nebulized DLPC-9-nitro camptothecin (DLPC-9NC) aerosol has demonstrated a lack of hematologic toxicity. While the aerosol doses administered were 3 to 5 times lower than those administered orally, blood levels were close to those observed after oral ingestion (29). The aerosol droplet size or MADD of the DLPC-9NC liposome, as defined herein, is in the range that optimizes alveolar deposition. Alveolar-capillary exchange of 9NC through the pulmonary vein (30) makes inhalation therapy a method of rapid and efficient sustained arterial delivery through the lung parenchyma. This allows for first pass presentation of 9NC to the cancer site. It is demonstrated herein that high levels of 9NC are found in the lungs at the end of treatment and that clearance of 9NC from the lungs is slower than from the plasma.

Administration of the nebulized liposomal aerosol via inhalation is relatively easy using a jet nebulizer; patients can be trained to self-administer at home using a portable machine. Local pulmonary effects were bothersome in a few patients, but no incapacitating interference with pulmonary function was noted despite the presence of substantial primary or metastatic cancer in the lungs. Although chemical pharyngitis was the most prevalent dose-limiting side effect, the mucosa of the bronchus was spared significant toxicity despite a decrease in FEV1. Chemical pharyngitis increased during administration but disappeared at the conclusion of the treatment. Use of bronchodilators and steroid inhalers ameliorated this side effect. Additionally, bronchospasm was also more pronounced inpatients with extensive pulmonary involvement with cancer.

The methods of the present invention have demonstrated the systemic absorption of 9-nitrocamptothecin after pulmonary administration. Additionally, a partial remission of an endometrial cancer with metastases to the liver has been effected. As such, it is contemplated that systemic delivery of an anti-cancer drug, e.g., one of the camptothecins, via inhalation of a liposomal aerosol containing the drug can be used to treat other than pulmonary cancers.

As described herein, the invention provides a number of therapeutic advantages and uses. The embodiments and variations described in detail herein are to be interpreted by the appended claims and equivalents thereof. The following examples are given for the purpose of illustrating various embodiments of the invention and are not meant to limit the present invention in any fashion.

EXAMPLE 1

Animal Models

Nude Mice: Swiss immunodeficient nude mice of the NIH-1 high fertility strain, bred and housed at the Stehlin Institute were used for these experiments (15).

Human Cancer Xenografts: Human heterotransplants were established in nude mice. For an implant, approximately 50 mg of wet weight of finely minced tumor in 0.5 ml of Eagles minimum essential medium was injected under the skin over the right dorsal chest region. The animals were started on treatment with the experimental drug about 10 days after implantation of tumors. Tumors of breast cancers were measured in two dimensions, i.e., area, with calipers, while colon cancers were measured in three dimensions, i.e., volume, with calipers.

EXAMPLE 2

Camptothecin Liposome Aerosol Formulation and Administration

CPT and 9-nitrocamptothecin were provided by Dr. Beppino Giovanella of the Stehlin Institute, Houston, Tex. DLPC was obtained from Avanti Polar Lipids, Pelham, Ala. Aerotech II nebulizers for animal studies were obtained from Cis-USA, Inc., Bedford, Mass.

For formulation of liposomes, 9-NC (100 mg/ml) or CPT (10 mg/ml) was dissolved in 100% DMSO, and added to DLPC dissolved in tertiary butanol (40° C.) so the final DMSO concentration did not exceed 5 percent of the total volume and the ratio of drug to lipid was 1:50 (w/w). The final suspension was clear. If precipitation occurred, it was reheated to 50-60° C. The preparation was frozen in liquid nitrogen and lyophilized overnight. For use the material was dissolved in sterile water to the appropriate drug concentration, not exceeding 1.0 mg/ml for either drug. The efficiency of incorporation of drug in the liposomes was examined qualitatively by microscopic examination under polarized light. Unincorporated drug was seen as bi-refringent crystals. The efficiency of incorporation was examined by centrifugation of aqueous suspensions of liposomes on Percoll™ gradients. One-tenth ml of suspension was layered over 2 ml of gradient and centrifuged at 2000 rpm for 25-30 minutes. Liposomes layer at the water-Percoll interface, while unincorporated drug was deposited at the bottom of the tube. Many other lipids may be substituted for DLPC in the formulation and use of liposomes for delivery of drugs by aerosol (26).

EXAMPLE 3

HPLC Analysis

The Waters (Milford, Mass.) 710B Wisp automatic injector and Waters Nova-Pak C18 column at room temperature was used to quantitate CPT and 9-NC. The mobile phase was 30% acetonitrile and 70% of 0.1% glacial acetic acid. CPT was detected using the Waters 470 scanning fluorescence detector set to an excitation wavelength of 370 nm and an emission wavelength of 440 nm. 9-NC was detected using the Waters 440 absorbence detector and monitoring at 254 nm. The data were analyzed with the Waters Millenium software.

EXAMPLE 4

Aerosol Droplet Measurement

The size of aerosol droplets was measured with the Andersen ACFM non-viable ambient particle sizing sampler (Andersen Instruments, Inc., Atlanta, Ga.) by methods previously described (33). Mass median aerodynamic diameters and geometric standard deviations were determined using KaleidaGraph 2.0 (Synergy Software, Reading Pa.). The aerosol droplets consisted of an aqueous suspension of liposomes. Liposome diameters were measured in aqueous suspension with the Model 3300 NICOMP Laser Particle Sizer.

EXAMPLE 5

Comparison of Plasma Concentrations of 9-NC After Oral Administration

Table 1 shows a comparison of blood or plasma concentrations of 9-NC and the time of peak concentrations following oral administration to humans, dogs and mice (34). Single oral doses ranged from 0.1 to 1.0 mg/kg for humans and dogs and were 4.1 mg/kg for mice. There may be some differences in pharmacokinetics between CPT and 9-NC, but it is a reasonable possibility that the foregoing differences are predictive of the properties of both agents.

Table 1

Comparison of 9-NC Concentrations in Blood or Plasma Following Single Oral, Intranasal or Aerosol Dosage

|       |                              | Blood or plasma concentration | Time of maximum concentration |
|-------|------------------------------|-------------------------------|-------------------------------|
|       | Oral dose (Single doses)     |                               |                               |
| Human | 0.1 mg/kg (7 mg/dose)        | 483 ng/ml                     | 3.4 h (T1/2 = 2.5 h)          |
|       | 1.0 mg/kg (70 mg/dose)       | 1247 ng/ml                    | 5.3 h (T1/2 = 4.9 h)          |
| Dog   | 1.0 mg/kg (10 mg/dose)       | 19.1 ng/ml                    | 0.7 h (T1/2 = 6.4 h)          |
| Mouse | 4.1 mg/kg (0.124 mg/dose) *Intranasal | 732 ng/ml            | 6 min (T1/2 = 10 h)           |
| Mouse | 233 µg/kg (7 µg/mouse) *Inhaled in liposome aerosol (30 min) | 213 ng/ml | end of instillation |
| Mouse | 16.2 µg/kg (486 ng/mouse)    | 13.9 ng/ml                    | end of aerosolization         |

*Intranasal and aerosol results from Baylor Aerosol Laboratory, the others from Hinz, H. R. (see text for reference)

Table 2 describes the method of calculating aerosol dosage in the mouse, and this is the basis for determining dosages cited in Table 1. Much of the inhaled drug is deposited in the nasopharynx of the mouse because of the complex nose structure of rodents. Similarly, nasal instillation leads to high nasopharyngeal deposition. Material deposited here is promptly transported to the esophageal orifice and swallowed. About 10-15 percent of the inhaled aerosol dose, however, will penetrate to the peripheral lungs.

In humans with mouth breathing, only small amounts of the aerosol particles will deposit in the mouth and virtually none will deposit in the nasopharynx. Material deposited in the central airways is returned to the pharynx by mucociliary action where it is swallowed. In the case of primary lung tumors, which often occur at bronchial bifurcations, drug will deposit on tumor surfaces and be adsorbed directly into the tumor mass. Material deposited beyond the 16th Weibel generation, which is beyond the ciliated epithelium, will not be moved upward; thus, in tumors within the peripheral lung parenchyma, the drug will deposit in adjacent areas and be absorbed directly into the tumor mass. In addition, a major advantage of the present invention is that drug deposited beyond the ciliated epithelium is picked up by capillaries in the interstitial space and the lymphatics of the lungs and will enter the circulation.

TABLE 2

Calculation of deposited doses of 9-NC in different species when administered by aerosol
NEBULIZER: AeroTech II; 10 L/min; Measured 1.7% efficiency
RESERVOIR: 9-Nitrocamptothecin (9NC)-DLPC liposomes: 100,500 or 1,000 µg 9NC/mL and 1:50 (w/w) mg DLPC/mL
Dose Calculation

| Species | Drug | MMAD | 9NC in Resv (µg/mL) | 9NC in Aerosol (µg/L) | Body Wt (kg) | Rx Time (min/day) | K* | Drug Dose (µg/kg/min) | Total Drug (µg/kg/day) | (µg/day) | Resp Secr (µg/mL)** | Weibel Generations: 0-16 (µg/mL)*** | 17-23 (µg/mL)*** |
|---|---|---|---|---|---|---|---|---|---|---|---|---|---|
| Human [adult] | 9NC | 0.8 | 100 | 1.8 | 70 | 15 | 0.076 | 0.14 | 2.0 | 142 | 0.68 | 1.4 | 5.8 |
| Human [adult] | 9NC | 0.8 | 100 | 1.8 | 70 | 30 | 0.076 | 0.14 | 4.1 | 284 | 1.35 | 2.7 | 11.7 |
| Human [adult] | 9NC | 1.2 | 500 | 8.5 | 70 | 15 | 0.076 | 0.64 | 9.6 | 675 | 3.21 | 6.5 | 27.7 |
| Human [adult] | 9NC | 1.2 | 500 | 8.5 | 70 | 30 | 0.076 | 0.64 | 19.3 | 1,353 | 6.44 | 13.0 | 55.5 |
| Human [adult] | 9NC | 1.5 | 1,000 | 15.9 | 70 | 15 | 0.076 | 1.20 | 18.0 | 1,259 | 6.00 | 12.1 | 51.6 |
| Human [adult] | 9NC | 1.5 | 1,000 | 15.9 | 70 | 30 | 0.076 | 1.20 | 36.0 | 2,518 | 11.99 | 24.2 | 103.3 |
| Dog | 9NC | 1.2 | 500 | 8.5 | 30 | 15 | 0.100 | 0.85 | 12.8 | 383 | 4.26 | 8.6 | 36.7 |
| Dog | 9NC | 1.2 | 500 | 8.5 | 30 | 30 | 0.100 | 0.85 | 25.6 | 767 | 8.52 | 17.2 | 73.4 |
| Cotton Rat | 9NC | 1.2 | 500 | 8.5 | 0.075 | 30 | 0.350 | 2.98 | 89.5 | 6.71 | 29.8 | | |
| Cotton Rat | 9NC | 1.2 | 500 | 8.5 | 0.075 | 60 | 0.350 | 2.98 | 178.9 | 13.42 | 59.6 | | |
| Cotton Rat | 9NC | 1.2 | 500 | 8.5 | 0.068 | 30 | 0.350 | 2.98 | 89.5 | 6.08 | 29.8 | | |
| Mouse | 9NC | 0.8 | 100 | 1.8 | 0.030 | 15 | 0.300 | 0.54 | 8.1 | 0.24 | 2.7 | | |
| Mouse | 9NC | 0.8 | 100 | 1.8 | 0.030 | 30 | 0.300 | 0.54 | 16.1 | 0.48 | 5.4 | | |
| Mouse | 9NC | 1.2 | 500 | 8.5 | 0.030 | 15 | 0.300 | 2.55 | 38.3 | 1.15 | 12.8 | | |
| Mouse | 9NC | 1.2 | 500 | 8.5 | 0.030 | 30 | 0.300 | 2.56 | 76.7 | 2.30 | 25.6 | | |
| Mouse | 9NC | 1.2 | 500 | 8.5 | 0.030 | 60 | 0.300 | 2.56 | 153.4 | 4.60 | 51.1 | | |
| Mouse | 9NC | 1.2 | 500 | 8.5 | 0.030 | 120 | 0.300 | 2.56 | 306.7 | 9.20 | 102.2 | | |
| Mouse | 9NC | 1.5 | 1,000 | 15.9 | 0.030 | 15 | 0.300 | 4.76 | 71.4 | 2.14 | 23.8 | | |
| Mouse | 9NC | 1.5 | 1,000 | 15.9 | 0.030 | 30 | 0.300 | 4.77 | 143.1 | 4.29 | 47.7 | | |

*K(human/adult): 0.108 L-min/kg × 0.7; Assuming Nose and mouth breathing, Mouth-only = ½
K(cotton rat): 0.7 L-min/kg × 0.5
K(mouse): 1 L-min/kg × 0.3
K(dog, golden): 0.2 L-min/kg × 0.5
**Estimated Peak after each treatment: secretion volume = 1 mL/kg
***Based on data from Patton (3570) and Philadelphia info; Mouth-only breathing in man

EXAMPLE 6

Tissue Distribution of Camptothecin After Inhalation of Liposomal Aerosol in Mice Table 3 shows the tissue distribution of CPT following 15 minutes of nebulization in DLPC liposome aerosol. The deposited dose was calculated to be 486 ng per mouse. The mean concentrations in lungs and liver were similar with smaller concentrations in the other sites examined. Table 4 shows tissue distributions over a period of one hour following intranasal instillation of 7 µg per mouse or 233 µg/kg. Drug was cleared promptly from the lungs so that 15 minutes after stopping nebulization only negligible amounts of drug were present in the lungs. Liver, kidney and spleen had substantial amounts of drug initially which gradually diminished through the one hour of study. Interestingly, blood concentrations were the least throughout the study. These studies indicate substantial immediate deposition of drug in the lungs with rapid clearance to the viscera. The amount of drug contributed by absorption from swallowed drug is uncertain.

Table 3

Tissue Distribution of CPT Following 15 Minutes Inhalation of CPT Liposome Aerosol

TABLE 3

Tissue distribution of CPT following 15 minutes inhalation of CPT liposome aerosol

| Animal | Organ | CPT (ng/gm) tissue |
|---|---|---|
| 1 | Lung | 52.0 |
| | Liver | 44.3 |
| | Spleen | 12.0 |
| | Kidney | 29.3 |
| | Blood | 7.1 |
| 2 | Lung | 48.0 |
| | Liver | 44.3 |
| | Spleen | 16.4 |
| | Kidney | 21.8 |
| | Blood | 8.3 |
| 3 | Lung | 27.0 |
| | Liver | 21.9 |
| | Spleen | 11.4 |
| | Kidney | 18.0 |
| | Blood | 22.6 |
| 4 | Lung | 77.5 |
| | Liver | 178.0 |

TABLE 3-continued

Tissue distribution of CPT following 15 minutes inhalation of CPT liposome aerosol

| Animal | Organ | CPT (ng/gm) tissue |
|---|---|---|
|  | Spleen | 25.0 |
|  | Kidney | 50.0 |
|  | Blood | 17.7 |
|  | MEAN (±SD) CPT (ng/gm tissue) | |
|  | Lung | 51.1 ± 20.7 |
|  | Liver | 72.1 ± 71.4 |
|  | Spleen | 16.2 ± 6.3 |
|  | Kidney | 29.8 ± 14.3 |
|  | Blood | 13.9 ± 7.5 |

The CPT concentration in the liposomal preparation in the nebulizer was 0.2 mg/ml aerosol was generated with an Aerotech II nebulizer operating at a flow rate of 10 L/min.

Table 4

Time Dependent Organ Distribution of CPT After Intranasal Administration

TABLE 4

Time dependent organ distribution of CPT after intranasal administration

| | | Time (minutes) | | |
|---|---|---|---|---|
| Organ | 0 | 15 ng/gm tissue | 30 | 60 |
| Lung | 1287 ± 657 | 19 ± 3 | 36 ± 23 | 7 ± 3 |
| Liver | 651 ± 418 | 255 ± 101 | 66 ± 17 | 34 ± 7 |
| Kidney | 542 ± 174 | 190 ± 57 | 49 ± 13 | 24 ± 21 |
| Spleen | 351 ± 137 | 84 ± 32 | 21 ± 8 | 7 ± 2 |
| Blood | 213 ± 19 | 53 ± 20 | 8 ± 3 | 4 ± 2 |

CPT was administered in liposomal formulation prepared with DLPC with initial drug concentration 0.2 mg/ml.

35 μL of suspension was installed to each animal (group of 3 animals was treated for each time point).

EXAMPLE 7

Distribution of Camptothecin in Blood and Viscera After Intramuscular Injection

Table 5 shows the distribution of drug in blood and viscera following intramuscular injection of CPT. Drug disappeared very slowly from the site of intramuscular injection in the first 12 hours, with only very small concentrations detected in the liver and virtually no drug present at other sites. Concentrations in the blood were negligible throughout the study. The dose administered was the same as that given by intranasal instillation. These findings indicate a speedier and more efficient systemic absorption of drug after pulmonary administration of drug than by the intramuscular route. It is likely that deposition in organs and vascular spaces will increase the opportunity for exposure to albumin molecules and degradation to the carboxyl form of the drug.

TABLE 5

Time dependent organ distribution of CPT after intramuscular administration

| | Time (minutes) | | | |
|---|---|---|---|---|
| Organ | 0 | 30 ng/gm tissue | 60 | 1200 |
| Lung | 2 ± 1 | 4 ± 2 | 3 ± 3 | 4 ± 3 |
| Liver | 3 ± 1 | 87 ± 74 | 136 ± 107 | 126 ± 116 |
| Spleen | 2 ± 1 | 18 ± 9 | 11 ± 5 | 5 ± 1 |
| Kidney | 2 ± 0 | 40 ± 14 | 26 ± 7 | 15 ± 5 |
| Blood | 2 ± 1 | 12 ± 5 | 8 ± 1 | 4 ± 1 |
| Site of inj. | 6918 ± 265 | 4309 ± 1548 | 4609 ± 1412 | 1544 ± 751 |

Remarks: CPT initial stock 5 mg/ml in DMSO was suspended in saline (1.4 μL stock + 48.6 μL saline) and total 50 μL of suspension was injected i.m. in each mice.
Group of 3 animals was treated for each time point.

EXAMPLE 8

Stability of Liposomes Consisting of DLPC and 9-NC

Table 6 shows the stability of liposomes with fixed weight ratio of 9-NC and DLPC of 1:50 (w/w) but with increasing concentrations of constituents from 0.1 mg/ml to 1.0 mg/ml of drug. The samples were tested under various conditions after vortexing, but before start of nebulization, after nebulization for 1.5 to 2 minutes (sample taken from the fluid in the reservoir of the nebulizer) and from the aerosol that was collected in an all-glass impinger (All-Glass Impinger, Ace Glass Co., Vineland N.J.).

TABLE 6

Liposome particle size and drug crystal formation in preparations of 9-NC DLPC liposome formulations

| Concentration (mg/ml) | | | Liposome particle | Crystals presence |
|---|---|---|---|---|
| 9NC | DLPC | Sample | size, nm | (visual estimation) |
| 0.1 | 5.0 | 1 | 8006 | − |
|  |  | 2 | 798 | + |
|  |  | 3 | 332 | − |
| 0.2 | 10.0 | 1 | 6201 | − |
|  |  | 2 | 434 | + |
|  |  | 3 | 812 | − |
| 1.0 | 50.0 | 1 | 5448 | ++ |
|  |  | 2 | 718 | ++ |
|  |  | 3 | 816 | + |

The most stable preparation was the one with lowest concentration of constituents. A few crystals appeared in the reservoir following nebulization. Nebulization caused a tenfold reduction in the diameter of the liposome particles, due to the shear forces associated with nebulization. There was further reduction in the diameter of liposome particles recovered from the aerosol. This finding is consistent with selection of smaller particles for discharge in aerosol. The lack of crystals suggests that crystals may not nebulize as readily as liposomes. With larger dosages of liposomes, size reduction following nebulization occurred, but particles recovered from aerosol were not reduced in size compared to particles that had been cycled in the reservoir of the nebulizer.

EXAMPLE 9

Figure 2:
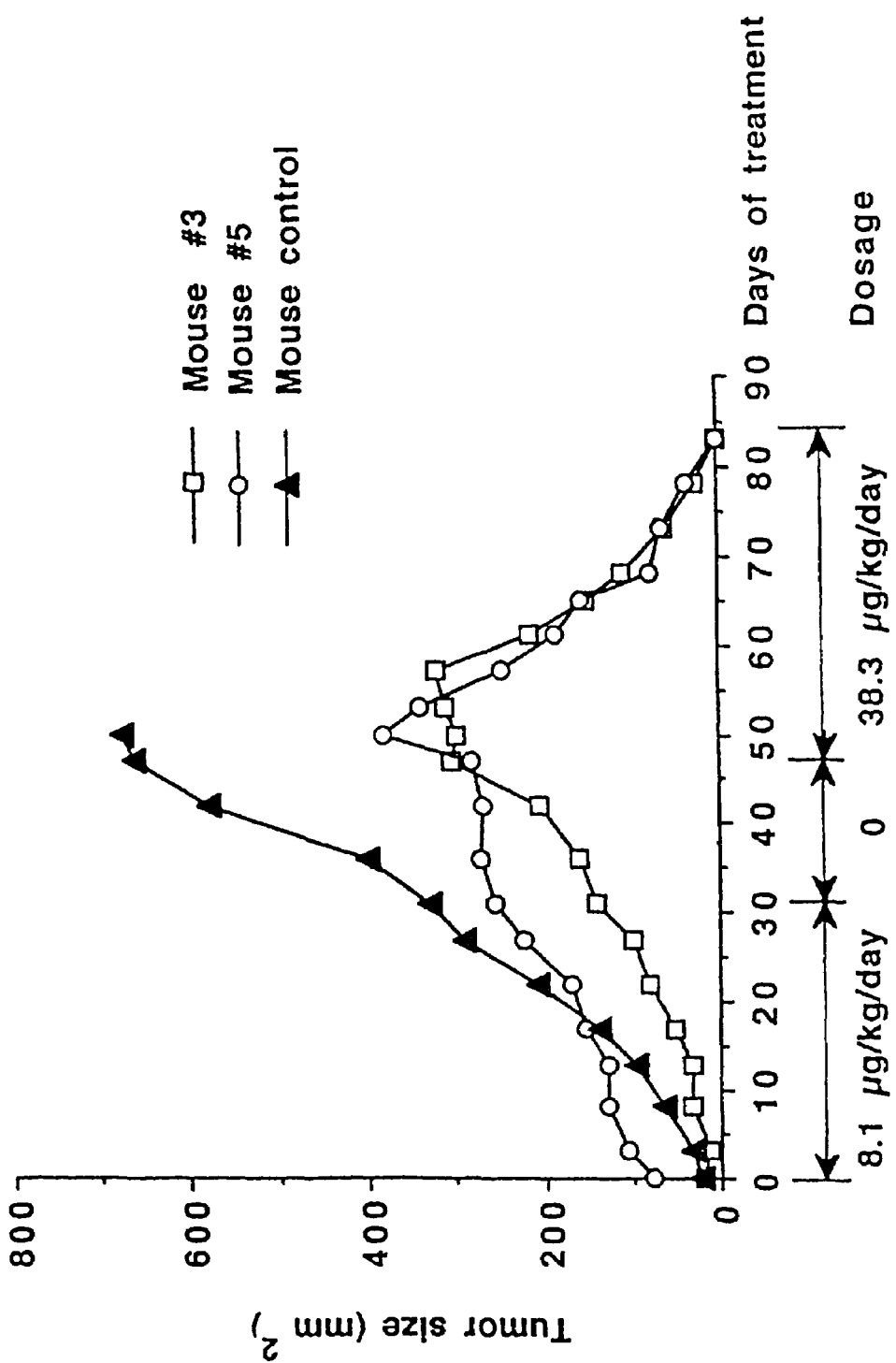
FIG. 2 demonstrates the effect of further treatment with 9-NC-DLPC liposome aerosol in mice selected from FIG. 1.

Effect of DLPC/9-NC Liposomal Aerosol on Growth of Human Breast Cancer Explants in Mice FIG. 1 shows growth in the area of subcutaneous breast cancer xenografts during treatment with 9-NC-DLPC liposome aerosol. There were six 9-NC treated and 5 control mice. Treatments were given 15 minutes daily, five days per week. The dose was 8.1 µg/kg per day. The deposited dose in the respiratory tract of each mouse was estimated to be 234 ng per day. The data on tumor size was normalized and the divergence of tumor size (% initial tumor growth) in the two groups was highly significant by day 17 of treatment ($P<0.011$). After this time, control mice were sacrificed because of the presence of large necrotic tumor masses. FIG. 2 shows the course of events with two treated mice which were subsequently followed with higher doses of drug, following a period of 16 days without treatment. A few days following restart of treatment with a five-fold increase in the dose of 9-NC liposome aerosol, the size of tumors in the treated animals diminished rapidly, and were no longer visible by the 85th day after start of treatment.

EXAMPLE 10

Figure 3:
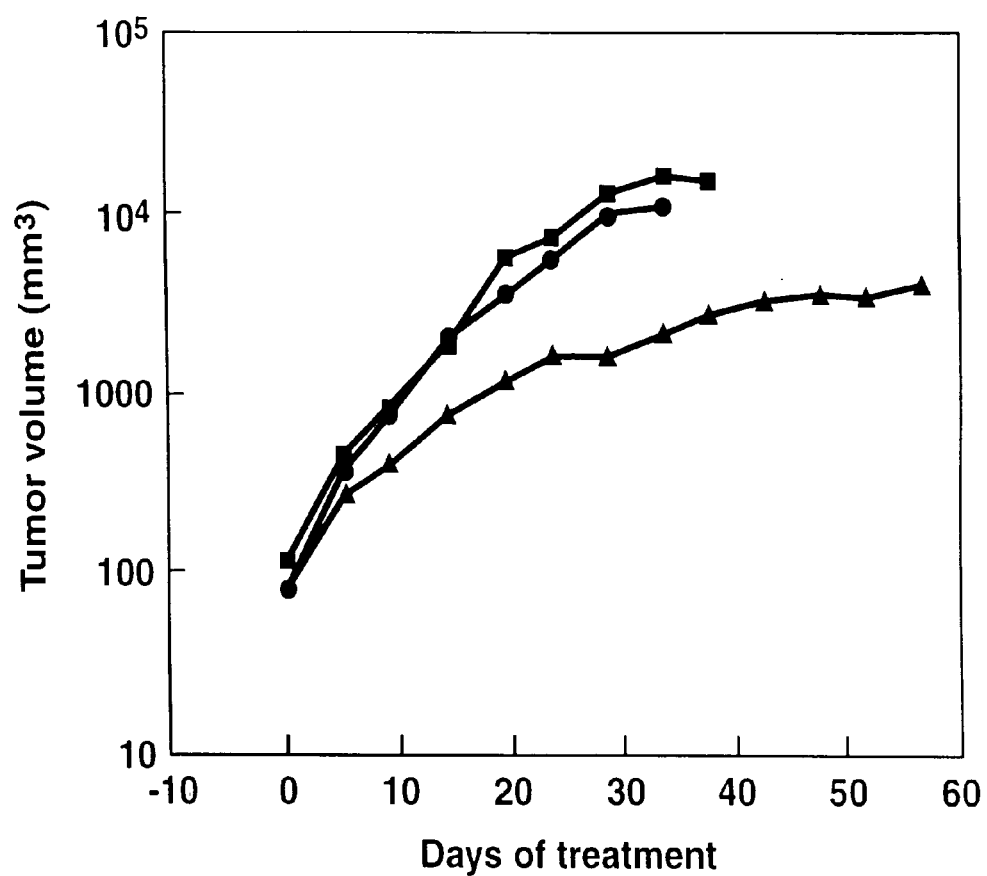
FIG. 3 demonstrates the effect of treatment with 9-NC-DLPC liposome aerosol on xenografted human colon cancer (Squires) in nude mice.

Effect of DLPC/9-NC Liposomal Aerosol on Human Colorectal Cancer Xenografts in Nude Mice A similar study was performed in nude mice with human colon carcinoma xenografts and is shown in FIG. 3. There were 15 treated and 20 control mice. Ten controls received empty DLPC liposomes and 10 received no treatment. Control animals that received no treatment or DLPC only showed a consistent and rapid increase in tumor size until they were sacrificed on day 36. The overall rate of tumor growth was 7 to 11 times greater in control than in 9-NC-treated mice.

The treated animals were divided into two groups of 10 each. One group received 77 µg/kg/daily, five days per week throughout the entire experiment. The other received 77 µg/kg per day five days per week until day 35 when the dose was increased to 153 µg/kg per day five days per week until day 46 when it was increased to 307 µg/kg on the same schedule until day 61. There was slightly less increase in tumor size in the group receiving the higher dose, but the differences were not statistically significant, and the data are combined in the figure.

Four mice in the DLPC treatment group were sacrificed because of large tumors or tumor necrosis before day 61, and six mice in the no treatment group were sacrificed for the same reasons before day 61. In the treatment group five mice were sacrificed because of tumor necrosis or emaciation before day 61. The emaciated mice were in the high dose group, suggesting drug toxicity. One additional treated mouse was sacrificed because of rectal prolapse. Based on these findings of reduced rate of tumor growth, day 28, ($P<0.007$, Student t test, 2 tailed) and reduced mortality there is an unequivocal therapeutic effect of 9-NC treatment ($P<0.002$~chi square test).

EXAMPLE 11

Figure 4:
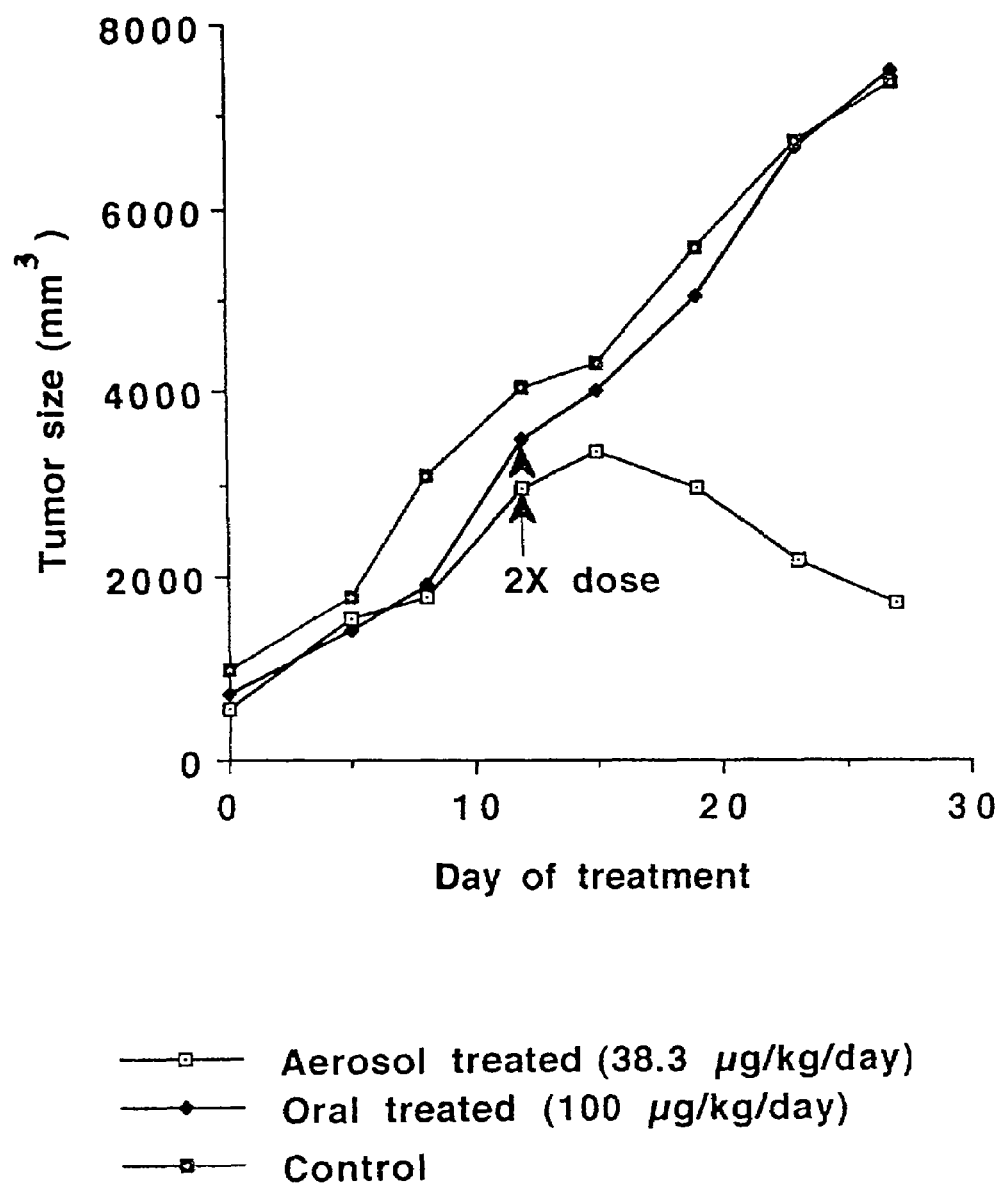
FIG. 4 demonstrates the effect of treatment with 9-NC-DLPC by liposome aerosol or by oral administration on the growth of human lung cancer xenografts (Spark) in nude mice as measured by tumor volume.

Effect of DLPC/9-NC Liposomal Aerosol on Human Lung Carcinoma Xenografts in Nude Mice Additionally, studies were performed on the effect of treatment with DLPC-9NC via liposome aerosol or via oral administration on the growth of human lung cancer xenografts (Spark) in nude mice as measured by tumor volume. Treatment was initiated about two weeks after tumor implantation. Control animals showed a rapid increase in volume of tumors. Animals who received oral dosage with the liposome drug aqueous suspension in doses of 100 µg/kg/day, which is more than twice the aerosol dosage, did not respond to treatment (FIG. 4).

Both aerosol and oral doses were doubled on day 13. The increased dosage was followed by decrease in the size of tumors treated with aerosol, but there was no decrease in size of tumors in mice given oral treatment. Thus, despite the fact that half or more of aerosol dosage administered to mice is deposited in the nose, head, trachea and upper bronchi and is promptly carried by the mucociliary system to the esophagus where it is swallowed, the fraction of inhaled drug that is deposited in the lung is principally responsible for the effect on tumor growth.

The most likely explanation of the clear efficiency of aerosol delivery is the rapid entry of the drug to the circulation where it is returned to the left heart, and then to the aorta and peripheral circulation. Thus, the drug would reach the tumors on "first pass" without having passed through the liver, which would remove large amounts of drug from blood.

EXAMPLE 12

Methods for a Phase I Clinical Trial Using an Aerosolized DLPC-9NC Liposome

Patients

The phase I clinical study was approved by the human-subject institutional review board. Patients 18 years of age or older, having provided informed sign consent, with primary or metastatic cancer in the lung, who had failed standard chemotherapy regiments and met specific criteria were eligible for the study. The patient must have a performance status of 0 to 2 according to the Eastern Cooperative Oncology Group Performance Status Scale, must be expected to survive more than 12 weeks and must have adequate bone marrow function, i.e., a granulocyte count of 1,500/mm$^3$ or more and a platelet count of 100,000/mm$^3$ or more and an absence of a regular red blood cell transfusion requirement. Additionally, the patient must have normal renal and hepatic functions, i.e., a serum bilirubin concentration lower than 2 mg/dl and SGOT or SGPT lower than twice the upper limit of normal. The patient must have no known respiratory disease other than cancer and pulmonary function of 50% or more of the predicted FEV$_1$, FEV$_1$/FVC, TLC, and DLCO values.

Patients were excluded if their disease was amenable to attempted curative therapy, if they had known symptomatic central nervous system metastases, other serious illness or psychiatric condition. A patient could not have received concurrent treatment with other experimental drugs or other anti-cancer therapy. Female patients were excluded if they were pregnant, lactating or not using effective contraception. Of the 25 patients studied, 24 completed the protocol. One patient refused further therapy after 15 minutes of aerosol. The characteristics of the 25 patients entered in the study are shown in Table 7.

TABLE 7

| Characteristics | Number of Patients |
|---|---|
| Age: | |
| Median: 55 years | |
| Range: 39-84 years | |
| Performance Status: | |
| 0 | 11 |
| 1 | 12 |
| 2 | 2 |
| Sex: | |
| Female | 18 |
| Male | 7 |
| Histology: | |
| Sarcoma | 3 |
| Melanoma | 3 |
| Endometrial cancer | 5 |
| Lung Cancer | 6 |
| Cervix Cancer | 4 |
| Pancreatic Cancer | 1 |
| Thyroid Cancer | 2 |
| Trophoblastic Cancer | 1 |
| Prior Chemotherapy: | 21 |
| Prior XRT: | 13 |
| Prior Surgery: | 14 |
| Other Characteristics | |
| Number of prior chemotherapy: | |
| 1 | |
| 2 | |
| $\geq 3$ | |

Treatment

This was a single-arm, non-randomized feasibility evaluation followed by a phase I trial of DLPC-9NC administered by aerosol five consecutive days per week. Six patients were entered in the feasibility cohort and treated twice for approximately 30 minutes per nebulization with 2 mg of 9NC in 10 ml of sterile water until the nebulizer reservoir was empty. This constitutes a daily dose of 6.7 µg/kg or 0.26 mg/m$^2$ followed by an observation period of 2 weeks (Phalen, 1984 #2552).

Once the feasibility of delivering chemotherapy by aerosol was established, the phase I study began first by increasing the number of weeks of delivery with one patient per each test period followed by 2 weeks of observation, i.e., 2, 4, then 6 consecutive weeks. Dose escalation started with 8 weeks of administration with 3 to 6 patients enrolled in each dose escalation cohort. Dose escalation was done first by doubling the concentration of drug in the nebulizer, then by increasing the amount of time per daily administration. The following doses per cohort were 6.7, 13.3, 20.0, and 26.6 µg/kg/day (Phalen, 1984 #2552) or 0.26, 0.52, 0.78, and 1.04 mg/m$^2$/day, respectively.

Drug was administered through an AeroMist nebulizer (CIS-US, Bedford, Mass.) flowing at 10 L of compressed air/min with a reservoir containing the DLPC-9NC preparation and administered through a mouth-only face-mask (Hans Rudolph Inc., Kansas City, Mo.). Patients and the aerosol nebulizer were enclosed in a HEPA-filtered airborne scavenging tent (Peace Medical Inc., Orange, N.J.). Premedications prior to starting aerosol treatment consisted of albuterol inhalers for three days, twice a day. Albuterol and fluticasone propionate inhalers were then prescribed on an as needed basis throughout the treatment. Prior to treatment patients were given the opportunity to simulate a treatment in order to familiarize themselves with the tent environment, facemask and respiratory techniques.

The first course and the first week of the second course of treatment were administered at M.D. Anderson Cancer Center under clinical supervision. This time was used to train patients, after which if no side effects greater than 2 were observed, patients were allowed to self administer treatment at home with a portable air compressor Easy Air 15® (Precision Medical, Northampton, Pa.) and an Enviracaire HEPA filtering system (Honeywell, Golden Valley, Minn.). Home treatment was supervised weekly by telephone contact and once by a home visit. Repeated courses at the same or the previous dose level were administered to the patients who benefited from the treatment, either remission or stabilization of disease. If toxic effects precluding therapy persisted for more than 3 weeks, the patients were taken off study.

At study entry and every three weeks a complete medical history was taken, a physical examination was performed and performance status was noted. Weekly complete blood cell count, and monthly relevant blood chemistgries and urinalysis were performed. Tumor markers and a CAT-scan of the chest were obtained at baseline and prior to each course. At the end of the study, all radiographic imaging data of responding patients were reviewed by an independent radiologist and by the principal investigator to confirm the patients' responses. Simple spriometry, DLCO, and lung volumes were performed according to American Thoracic Society standards. Results were expressed as a percentage of the value predicted based on age and height according to the methods of Knudson et al. (11), before and following predefined aerosol exposures to detect possible pulmonary functional abnormalities. More frequent pulmonary function tests were performed at the principal investigators' discretion. Pulse oximeter readings were performed at intervals during daily treatments.

Pharmacological Procedures

The purpose of quantitation of 9NC from plasma and bronchoalveolar fluids was to determine systemic absorption from the alveolar-capillary exchange surface. Plasma concentrations of total 9NC and the lactone form were measured. For patients who volunteered for pharmacokinetic studies, blood was obtained at various time pints from the start of the aerosol treatment depending on the cohort. For cohort 1 used in the feasibility study blood was obtained at the end of the first week of treatment. Samples were taken at 0, 0.5, 1, 1.25, 1.5, 2, 3, 5, 7, and 24 hours from the start of the 1-hr aerosol exposure. For all other cohorts, samples were obtained at 0, 2, 5, 8, and 24 hours on days 1 and 5 of weeks 1, 4 and 8 where appropriate. Quantitation was performed either by LC/MS, for cohorts 1 and 2, or by HPLC analysis, for cohorts 3 to 6. 9NC plasma concentrations were calculated from the ratio of 9 NC to CPT as internal standard. Extraction of 9NC and its lactone form was performed using Waters C18 Sep-Pak Light cartridges immediately after separating the plasma by a method similar to that previously described (12). Minimal level of detection of 9NC/ml of plasma was 0.5 ng by LC/MS and 1.0 ng by HPLC.

Bronchoscopy was performed by a pulmonologist to obtain either bronchoalveolar lavage (BAL) fluid or bronchial aspirate for quantitation of 9NC. A BAL of the right middle lobe was performed once on volunteering patients at various times after the completion of treatment to study the amount of 9NC retained over time. Concentration of total 9NC in the BAL fluid was corrected for dilution by determining the ration of BUN in the lavage and in a plasma sample taken at the same time (13).

Criteria for Response and Toxicity

Toxicity was evaluated for each dose level during the first course of therapy to determine the DLT, which were based on the NCI Common Toxicity Criteria version 2 (http://ctep.cancer.gov/forms/CTCv20_4-30-992.pdf) and defined as the dose that produced a reversible grade 3 or 4 hematological toxicity lasting >7 days, or a reversible grade $\geq 3$ (grade 2 for neurotoxicity) non-myelosuppressive toxicity in >33% of patients treated at a given dose level. While the main purpose of this study was to determine the appropriate starting dose for phase II studies and to determine a toxicity profile for DLPC-9NC, clinical responses were determined according to the WHO criteria (14).

EXAMPLE 13

Determination of a Phase II Dose of Aerosolized Liposomal 9NC

If no DLT was observed among the initial 3 patients placed on a dosage level in Example 12, the dose was escalated by successive cohorts of 3 patients. If one instance of grade >3 toxicity was observed among the initial 3 patient, an additional 3 patients were treated at that level. If no further instances of grade >3 toxicity were observed, the dose was escalated for the next cohort of 3 patients. If at any time 2 patients in one cohort developed a grade >3 toxicity, entry onto this cohort was terminated. The recommended dose for phase II study was defined to be the highest dose for which no patient developed a grade >3 toxicity.

Pulmonary function was compared by the two-tailed, paired t-test to evaluate changes during and after treatment from baseline values. Total 9NC concentrations in plasma between cohorts were compared by two-tailed t test where possible.

Figure 5A:
FIG. 5A depicts the mucosa of the pharynx in a patient displaying chemical pharyngitis at dose limiting toxicity.
Figure 5B:
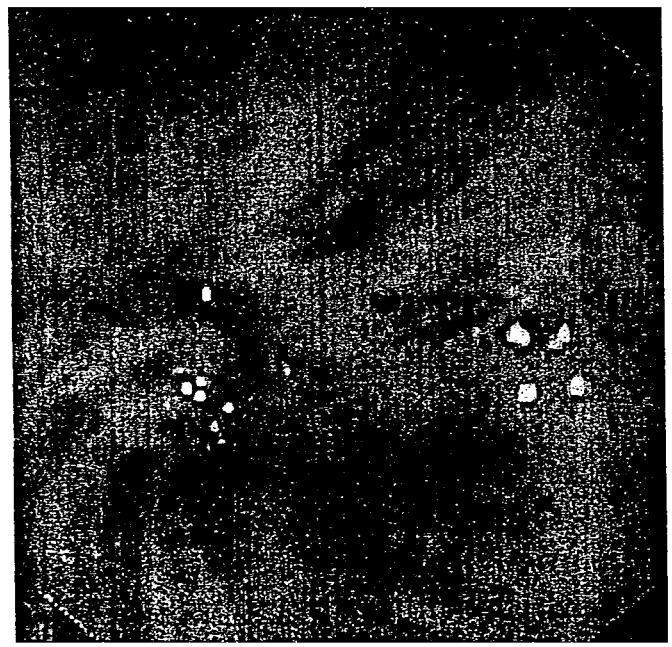
FIG. 5B depicts the mucosa of the bronchus in a patient during treatment

At 1.04 mg/m²/day with twice a day dosing the DLT was a chemical mucositis of the pharynx seen at the end of the first week in 2 patients (FIGS. 5A-5B). No changes in pulmonary function were observed in these patients. This cohort was halted and a new cohort at a dose of 0.78 mg/m²/day was opened. Five patients were entered at that level. One of these patients declined further therapy after 1 week. Two of the remaining four patients completed treatment with few side effects, but 2 patients required a dose reduction for grade 2 and 3 fatigue after 4 weeks of treatment. At dose of 0.52 mg/m²/day, all patients tolerated the treatment well.

Most side effects were grade 1. Table 8 shows the main side effects, with cough in 67% of patients, wheezing and chest congestion in 46%, sore throat in 33%, nausea in 62%, vomiting in 33%, anorexia in 33%, dysgeusia in 33%, fatigue in 50%, anemia in 29%, and skin rash around the face mask in 21%. Grade 1 epistaxis, chills, dysuria, and thrombocytopenia were seen in 4 patients or less. Table 9 shows the toxic effects for each patient cohort. Seven patients, who had benefited from the first course of therapy received one or more courses at home. No cumulative toxic effects were noted in these patients.

TABLE 8

Percentage of side effect per cohort (N = 24 patients)

| Side Effect | Cohort 1 (N = 9) | Cohort 2 (N = 3) | Cohort 3 (N = 5) | Cohort 4 (N = 2) | Cohort 6 (N = 5) |
|---|---|---|---|---|---|
| Cough | 33 | 100 | 100 | | 100 |
| Wheezing/Chest Congestion | 33 | 66 | 40 | | 80 |
| Sore Throat | 33 | 33 | 40 | 100 | |
| Dysgueusia | 22 | 66 | 20 | 50 | 40 |
| Anorexia | 44 | 66 | 20 | | 20 |
| Nausea | 55 | 66 | 80 | 50 | 60 |
| Vomiting | 22 | 33 | 40 | 50 | 40 |
| Epistaxis | | | 20 | | 40 |
| Peribuccal rash | | | 40 | 50 | 40 |
| Fatigue | 55 | 66 | 40 | 50 | 40 |
| Chills | 22 | 33 | | 50 | |
| Dysuria | | 33 | | | 20 |
| Anemia | 33 | | 40 | 50 | 20 |
| Thrombocytopenia | 11 | | | 50 | |

TABLE 9

Percentage of side effects per cohort (N = 24 patients)

| Side Effect | Grade 1 | Grade 2 | Grade 3 | Total (N, %) |
|---|---|---|---|---|
| Cough | 11 | 5 | | 16 (66%) |
| Wheezing/Chest Congestion | 6 | 5 | | 11 (46%) |
| Sore Throat | 6 | 1 | 1 | 8 (33%) |
| Dysgueusia | 8 | | | 8 (33%) |
| Anorexia | 7 | 1 | | 8 (33%) |
| Nausea | 6 | 8 | 1 | 15 (62%) |
| Vomiting | 6 | 2 | | 8 (33%) |
| Epistaxis | 3 | | | 3 (12%) |
| Peribuccal rash | 4 | 1 | | 5 (12%) |
| Fatigue | 6 | 5 | 1 | 12 (50%) |
| Chills | 4 | | | 4 (16%) |
| Dysuria | 2 | | | 2 (8%) |
| Anemia | 3 | 4 | | 7 (28%) |
| Thrombocytopenia | 2 | | | 2 (8%) |

Figure 6:
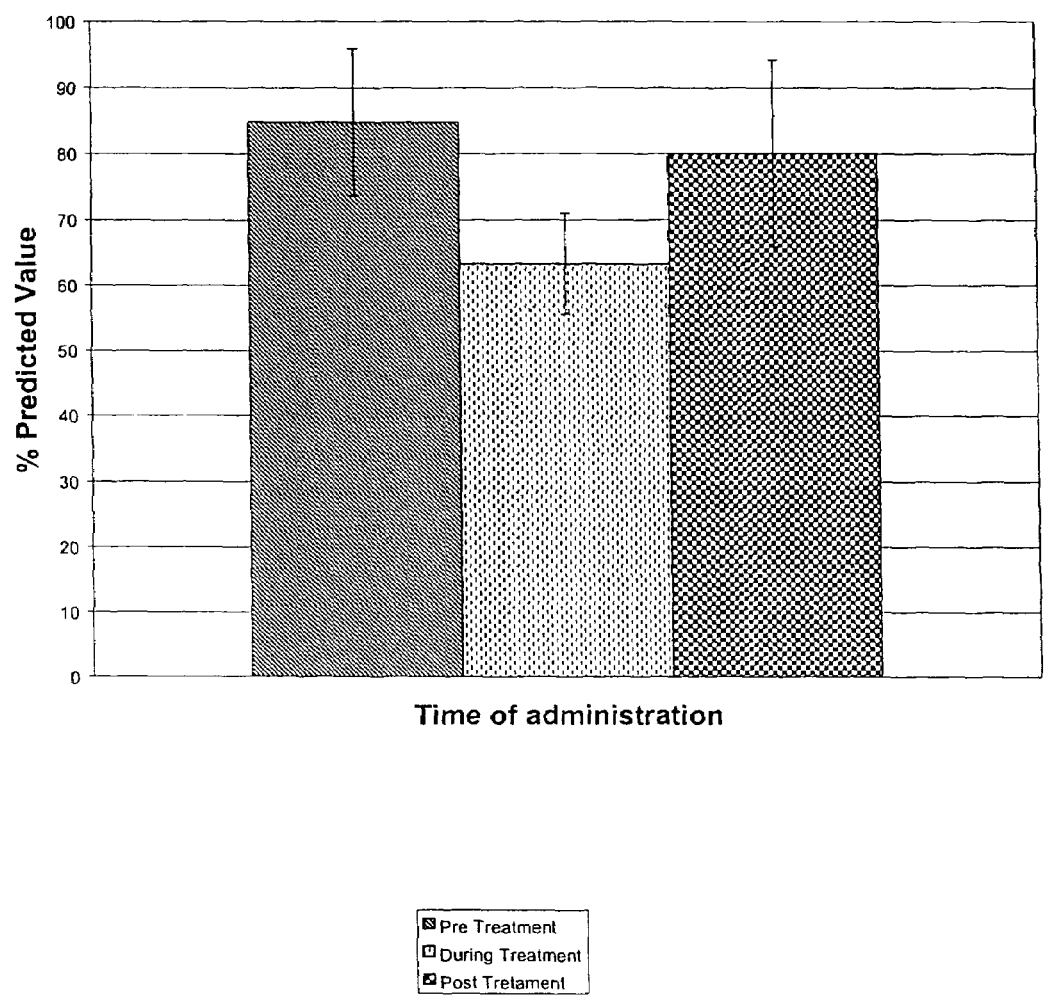
FIG. 6 depicts $FEV_1$ function during aerosol treatment. First bar is the baseline mean $FEV_1$ pre-treatment value. Second bar is the mean of the worst $FEV_1$ value per patient recorded during treatment. The last bar is the mean of the $FEV_1$ value per patient recorded two weeks after the end of the aerosol treatment.

FIG. 6 shows the effect of the aerosol chemotherapy on $FEV_1$. Mean $FEV_1$ and other pulmonary functions before treatment were at least 85 percent or more of predicted values. There was a decrease in pulmonary function for all tests (p<0.01; paired t-test, two-tailed). Except for 3 patients, the greatest reductions for $FEV_1/VC$, TLC, DLCO, and $O_2$ saturation remained within an acceptable clinical range (>50% predicted value). The 3 patients with a FVC and $FEV_1$<50% of predicted value at the end of treatment had extensive pulmonary involvement by tumors, which were progressive despite therapy. Mean $FEV_1$ function dropped by 22% during aerosol therapy (p<0.0001) and improved to 81% of predicted value upon cessation of therapy. The mean end treatment value was significantly different than the baseline (p<0.035; paired t-test, two-tailed), but remained in a range that is not clinically pathological (mean $FEV_1$=81% of predicted value). Lung function of the 24 enrolled patients is shown in Table 10.

TABLE 10

Lung function of the enrolled patients (N = 24)

| % Predicted Value | FVC | | | FEV₁ | | | FEV₁/VC | | | TLC | | | DLCO | | |
|---|---|---|---|---|---|---|---|---|---|---|---|---|---|---|---|
| | BL | Max | End | BL | Max | End | BL | Max | End | BL | Max | End | BL | Max | End |
| >75% | 17 | 5 | 12 | 15 | 3 | 12 | 23 | 15 | 22 | 23 | 10 | 11 | 17 | 5 | 13 |
| 50-75 | 7 | 10 | 8 | 9 | 9 | 7 | | 1 | | | 1 | 2 | 6 | 8 | 6 |
| <50% | | 1 | 2 | | 4 | 3 | | | | | | 1 | | | |
| ND | | 8 | 2 | | 8 | 2 | 1 | 8 | 2 | 1 | 13 | 10 | 1 | 11 | 5 |

Figure 7A:
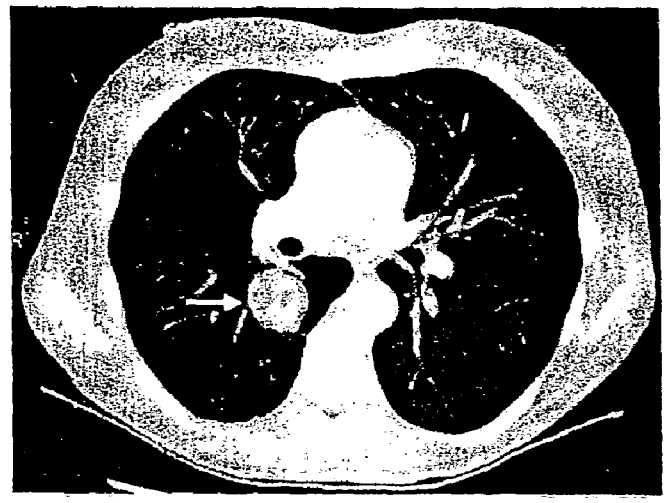
FIG. 7A depicts partial response in a lung metastasis of endometrial cancer after treatment.
Figure 7A:
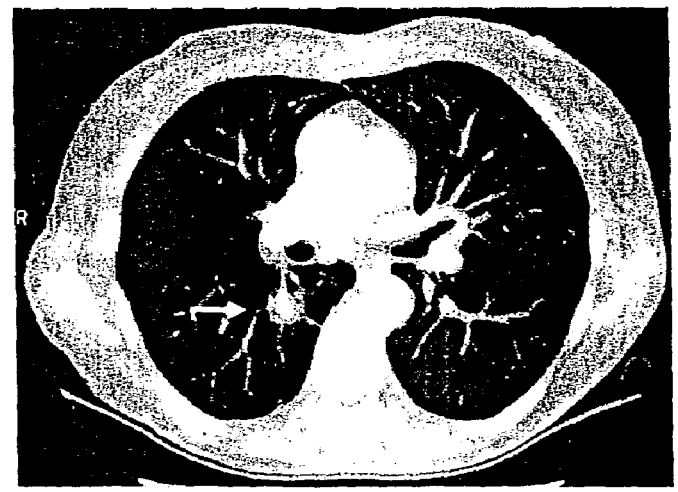
Figure 7B:
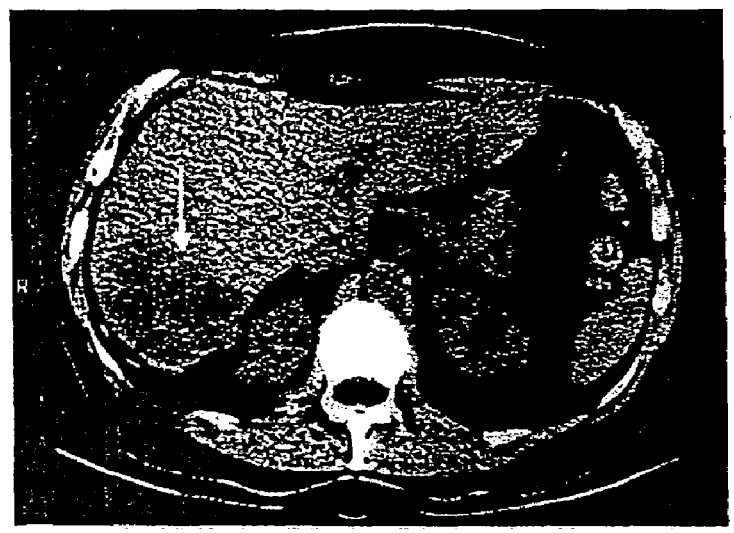
FIG. 7B depicts partial response in a liver metastasis of endometrial cancer after treatment.
Figure 7B:
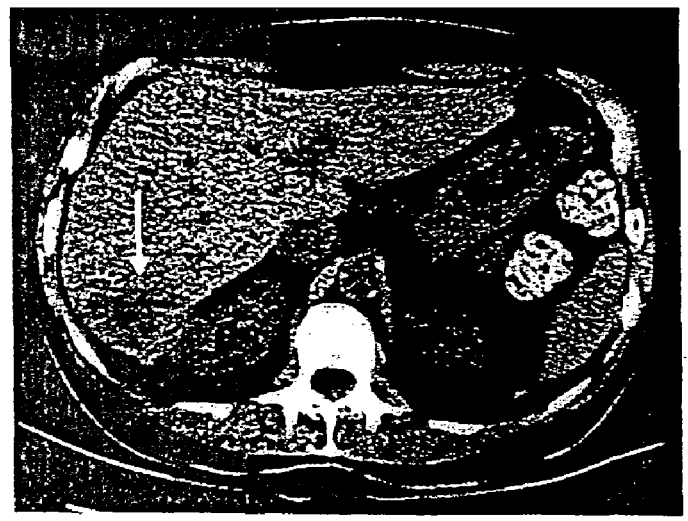

A partial remission was observed in 2 patients with endometrial carcinoma (FIG. 7A). Sustained responses occurred early after initiation of chemotherapy, within the first 4 weeks, and led to resection of pulmonary disease with curative intent in 2 patients. After resection these 2 patients received two courses of adjuvant chemotherapy with a combination of intravenous cisplatin and irinotecan, another camptothecin derivative. In another patient with endometrial cancer and liver metastases, a partial remission was observed in the liver, demonstrating the systemic potential of aerosol delivery of this drug (FIG. 7B).

Figure 8:
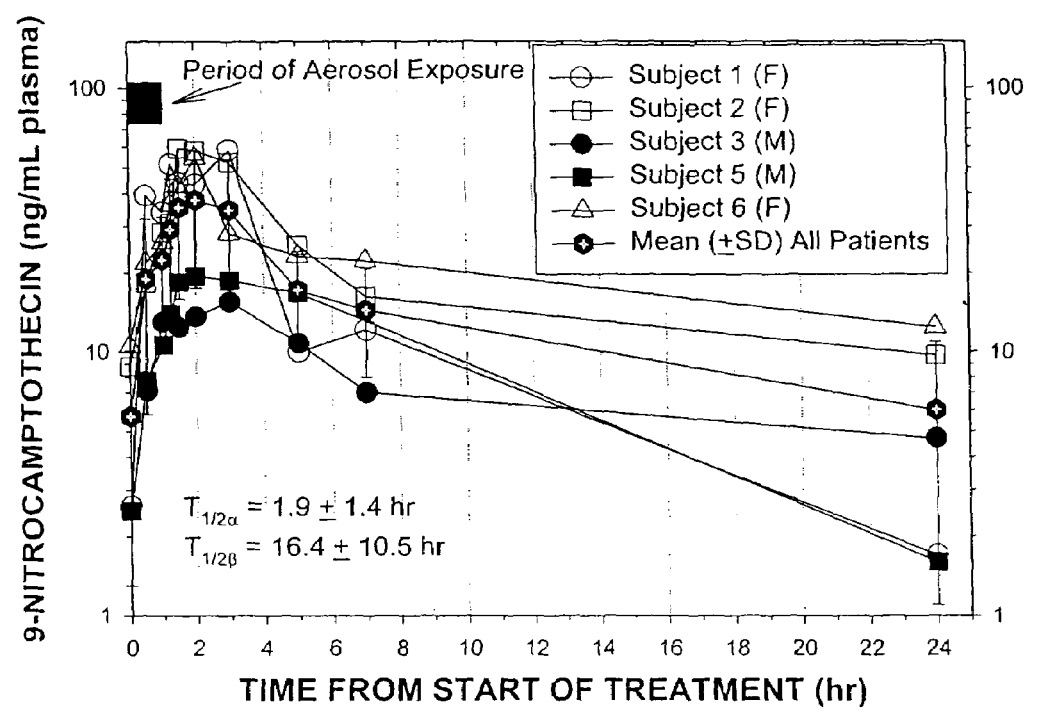

Of the six patients in cohort 1 (0.26 mg/m²), five volunteered for pharmacokinetic studies. With the last two patients, samples were processed within 3-5 min. to separate 9NC into its lactone form. 9NC measured as total 9NC was detected in plasma at the first time point, midway through the 1-hour aerosol exposure (FIG. 8). Total 9NC plasma concentrations continued to increase for 2 to 3 hr from the start of treatment reaching a mean (±SD) peak concentration of 37.7±20.2 ng/ml at 2 hr (range: 13.6-58.0 ng/ml). Mean (±SD) clearance of 9NC was biphasic with a $T_{1/2\alpha}$ of 1.9±1.4 hr and a $T_{1/2\beta}$ of 16.4±10.5 hr. The area under the curve of the lactone form measured in the last two patients comprised only 3.2 and 3.5% of the total 9NC (data not shown).

Four of the 5 patients above also volunteered to have either a BAL (3 patients) or a bronchial aspirate sample (1 patient) taken to measure pulmonary 9NC concentrations. The time of obtaining a sample as spread out among the patients from 1.2 to 4.8 hr from the start of aerosol treatment is shown in Table 11. Because of the large dilutions, BUN levels in the BAL fluids were below detection (i.e., <0.5 mg/dl). For the BAL fluids, 9NC concentrations were >4.2 to >10.6 times higher that those measured concurrently in the plasma (samples obtained between 2.1 to 4.8 hr from the start of aerosol treatment). For the bronchial aspirate taken almost immediately after the end of treatment, the ratio was 1.4.

TABLE 11

Total 9-Nitrocamptothecin in bronchoalveolar lavage (BAL) Fluids and a lung aspirate compared to plasma in subjects from cohort 1 receiving 9NC liposome aerosol for one hour (0.26 mg/m²)

| Subject No. | BAL Performed | | Time (hr)[1] | BUN (mg/dl)[2] | | 9NC (ng/ml) | | | BAL: Plasma Ratio |
|---|---|---|---|---|---|---|---|---|---|
| | Cycle | Day | | BAL | Plasma | BAL | Correct BAL[3] | Plasma[4] | |
| 1 | 1 | 3 | 2.1 | <0.5 | 11 | 8.2 | >180 | 43.2 | >4.2 |
| 3 | 4 | 3 | 4.8 | <0.5 | 13 | 4.3 | >112 | 10.8 | >10.4 |
| 4 | 2 | 4 | 3.5 | <0.5 | 7 | 25.8 | >361 | 34.2 | >10.6 |
| 6[5] | 1 | 4 | 1.2 | 13 | 11 | 60.7 | 51 | 36.2 | 1.4 |

Figure 9:
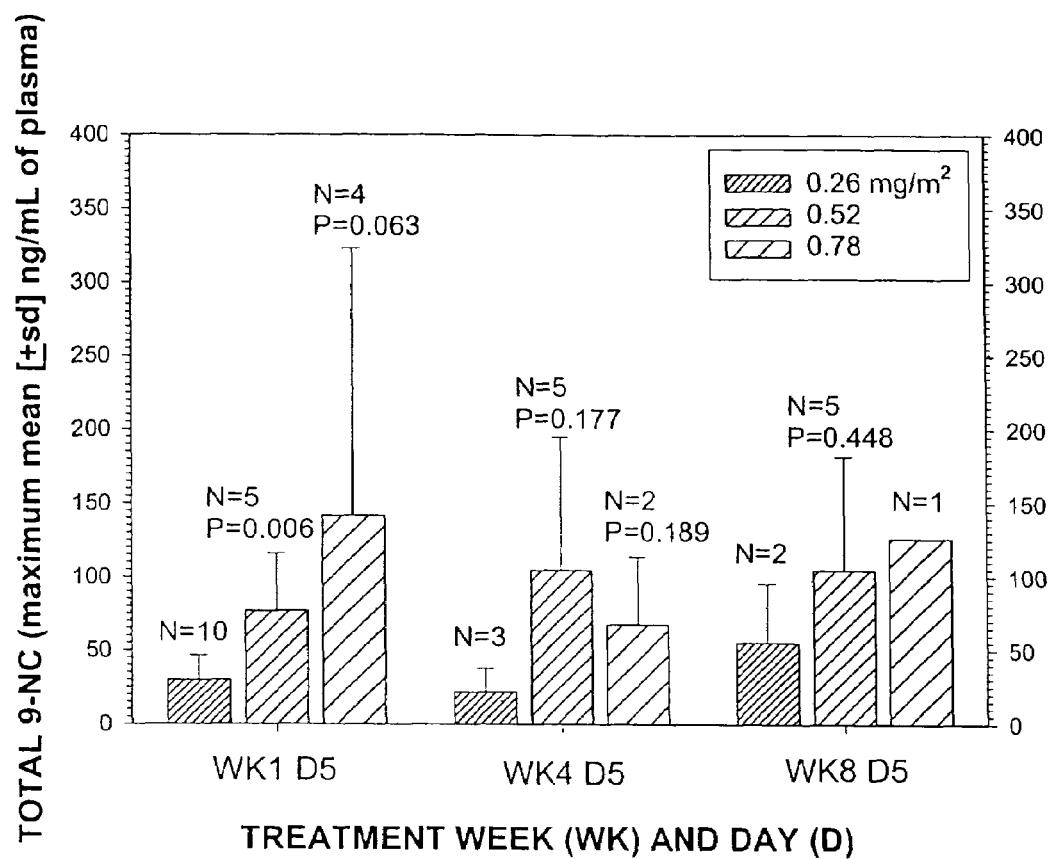
FIG. 9 demonstrates the effect of DLPC-9NC liposomal aerosol dosage on maximum total 9NC concentration ($C_{max}$) in plasma during 8 weeks of treatment for all cohorts. First group of bars is the mean $C_{max}$ after one week of treatment. Second group of bars is the mean $C_{max}$ after four weeks of treatment. Last group of bars is the mean $C_{max}$ after eight weeks of treatment.

[1]Time from start of aerosol treatment
[2]Minimum level of detection was 0.5 mg/dl
[3]Corrected from the ratio of BUN in plasma compared to BAL fluid
[4]Taken at the same time as the BAL specimen
[5]For subject 6, a lung aspirate was obtained To compare the effect of estimated deposited 9NC dosage on plasma drug levels, common time points were selected for cohorts, 1, 1B, 2, 3 and 6. A comparison of plasma drug levels at 0 (before start of treatment), 2 and 5 hr from the start of aerosol treatment is shown in FIG. 9. At doses of 0.26 and 0.52 mg/m², maximum mean plasma levels of total 9NC were directly proportional to the dose at the end of a week of treatment measured at 1, 4 and 8 weeks. Because of fewer patients at the 0.78 mg/m² dose, 9NC levels appeared higher, but were not statistically different. There appeared to be a sex different in total 9NC plasma levels for the first cohort on days 5 of the first week of treatment. Peak plasma levels in women of cohort 1 at the end of the first week of treatment were higher than for the men (P=0.046; t-test, two-tailed). A similar trend was observed at other time points for all cohorts.

THE FOLLOWING REFERENCES ARE CITED HEREIN

1. Ramsey et al., N Eng J Med 1993; 328:1740-6.
2. Skyler et al., Lancet 2001; 357:331-5.
3. Gilbert B E. J Aeros Med-Deposit Clear Effects Lung 1996; 9:111-22.

4. Gilbert et al., Am J Resp Crit Care Med 1997; 156:1789-93.
5. Gilbert et al., Inhal Toxicol 2001; 14:185-197.
6. Knight et al., Cancer Chemoth Pharmacol 1999; 44:177-86.
7. Koshkina et al., Proc Am Assoc Cancer Res 1998; 39:A1902.
8. Blaney et al., Cancer Chemoth Pharmacol 1998; 41:464-8.
9. Knight et al., Transact Am Clin Climatol Assoc 2000; 111:135-45.
10. Knight et al., Ann NY Acad Sciences 2000; 922:151-63.
11. Knudson et al., Am Rev Resp Dis 1983; 127:725-734.
12. Verschraegen et al., Anti-Cancer Drugs 1999; 10:375-83.
13. Rennard et al., J Appl Physiol 1986; 60:532-538.
14. Miller et al., Cancer 1981; 47:207-214.
15. Giovanella et al., Cancer Res 1991; 51:3052-5.
16. Garcia-Carbonero et al., Clin Cancer Res 2002; 8:641-661.
17. Mi et al., Biochem 1995; 34:13722-8.
18. Ahmed et al., Cancer Chemoth Pharmacol 1996; 39:122-30.
19. Hochster et al., J Clin Oncol 1994; 12:553-9.
20. Verschraegen et al., Ann NY Acad Sciences 2000; 922:237-46.
21. Abang et al., Sem Hematol 1998; 35:13-21.
22. Chourpa et al., Biochem 1998; 37:7284-91.
23. Hausheer et al., Proc Annu Meet Am Assoc Cancer Res 1997; 38:A1526.
24. Hertzberg et al., J Medic Chem 1989; 32:715-20.
25. Lesueur-Ginot et al., Cancer Res 1999; 59:2939-43.
26. Sugarman et al., Cancer Chemoth Pharmacol 1996; 37:531-8.
27. Koshkina et al., Cancer Chemoth Pharmacol 1999; 44:187-92.
28. Zamboni et al., Proc Am Soc Clin Oncol 2001: A411.
29. Verschraegen et al., Anti-Cancer Drugs 1998; 9:36-44.
30. Weibel E. Geometry and Dimensions of Airways of Conductive and Transitory Zones. Morphometry of the Human Lung. NY: Academic Press Inc., 1963:110-140.
31. Hallman, M., et al. N. Eng. J. Med. 1992 326:1233-1239.
32 Knight, V. and Waldrep, J. C. Liposome Aerosol for Delivery of Asthma Medications; see also In Kay, B., Allergy and Allergic Diseases, 1997, Blackwell Publications, Oxford, England, Vol. I pp. 730-741.
33. Waldrep, J. C. et. al., J Aerosol Med. 1994 7:135-145.
34. Hinz, H. R., et. al. Cancer Research. 1994 54:3096-3100.

Any patents or publications mentioned in this specification are indicative of the levels of those skilled in the art to which the invention pertains. Further, these patents and publications are incorporated by reference herein to the same extent as if each individual publication was specifically and individually incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for treating a primary lung cancer or a metastatic cancer to the lung in an individual comprising the step of:
delivering at least once to the respiratory tract of the individual via inhalation a nebulized liposomal aerosol comprising a dilauroylphosphatidylcholine liposome containing camptothecin or a derivative thereof in an amount sufficient to deliver a pharmacologically effective dose of said camptothecin or derivative thereof to treat said cancer, wherein said dose of camptothecin or derivative thereof delivered via inhalation is about 0.26 mg/m$^2$/day to about 1.04 mg/m$^2$/ day.

2. The method of claim 1, wherein said nebulized liposomal aerosol is delivered via an inhalation regimen comprising twice a day for 5 consecutive days within a week for one or more consecutive weeks.

3. The method of claim 2, wherein a period of consecutive weeks is the first 8 weeks out of a 10 week period.

4. The method of claim 3, wherein the inhalation regimen is repeated after week 10.

5. The method of claim 2, wherein said nebulized liposomal aerosol is inhaled for 60 minutes during each period of inhalation in the regimen.

6. The method of claim 1, wherein concentration of said camptothecin or derivative thereof in said dilauroylphosphatidylcholine liposome comprising said liposomal aerosol does not exceed 1.0 mg/ml.

7. The method of claim 6, wherein the concentration of said camptothecin or derivative thereof in said dilauroylphosphatidylcholine liposome comprising the liposomal aerosol is about 0.4 mg/ml.

8. The method of claim 1, wherein a ratio of camptothecin or derivative thereof to dilauroylphosphatidylcholine in said liposome comprising the liposomal aerosol is about 1:10 to about 1:50 wt:wt.

9. The method of claim 1, wherein said camptothecin derivative is 9-nitro-camptothecin, 9-amino-camptothecin or 10,11-methylenedioxy-camptothecin.

10. The method of claim 1, wherein said metastatic cancer is a sarcoma, a melanoma, lung cancer endometrial cancer, cervical cancer, pancreatic cancer, thyroid cancer or trophoblastic cancer.

11. The method of claim 1, wherein said liposomal aerosol is produced by the following steps:
dissolving said camptothecin or derivative thereof in a volume of DMSO to produce dissolved camptothecin or derivative thereof;
dissolving dilauroylphosphatidylcholine in an appropriate solvent to produce a dissolved dilauroylphosphatidylcholine;
combining said dissolved camptothecin or derivative thereof and said dissolved dilauroylphosphatidylcholine to produce a solution, said solution having a DMSO concentration not exceeding about 5% of the total volume of said solution wherein a weight ratio of said camptothecin or derivative thereof to said dilauroylphosphatidylcholine in said solution is in a range of about 1:10 wt:wt to about 1:50 wt:wt of said solution;
evaporating said solvents from said solution to produce a powder; and
redissolving said powder in sterile water to produce a suspension, wherein a concentration of said camptothecin or derivative thereof in said sterile water does not exceed said 1.0 mg/ml.

* * * * *

UNITED STATES PATENT AND TRADEMARK OFFICE
CERTIFICATE OF CORRECTION

| | | |
|---|---|---|
| PATENT NO. | : 7,348,025 B2 | Page 1 of 1 |
| APPLICATION NO. | : 10/663573 | |
| DATED | : March 25, 2008 | |
| INVENTOR(S) | : J. Vernon Knight et al. | |

It is certified that error appears in the above-identified patent and that said Letters Patent is hereby corrected as shown below:

In title page, item (63) Related U.S. Application Data, line 4, after "abandoned", please insert --which is a division of application No. 08/933,254, filed on September 23, 1997, now U.S. Patent No. 6,090,407--.

Signed and Sealed this

Twenty-fourth Day of June, 2008

JON W. DUDAS
*Director of the United States Patent and Trademark Office*